US012136494B2

(12) United States Patent
Calicchia

(10) Patent No.: US 12,136,494 B2
(45) Date of Patent: Nov. 5, 2024

(54) SYSTEM AND METHOD OF TRACKING AND GRAPHICALLY REPRESENTING TEST RESULTS

(71) Applicant: Food Microbiological Laboratories, Inc., Cypress, CA (US)

(72) Inventor: Melissa Calicchia, Cypress, CA (US)

(73) Assignee: Food Microbiological Laboratories, Inc., Cypress, CA (US)

( * ) Notice: Subject to any disclaimer, the term of this patent is extended or adjusted under 35 U.S.C. 154(b) by 538 days.

(21) Appl. No.: 17/407,091

(22) Filed: Aug. 19, 2021

(65) Prior Publication Data

US 2022/0059241 A1 Feb. 24, 2022

Related U.S. Application Data

(60) Provisional application No. 63/067,845, filed on Aug. 19, 2020.

(51) Int. Cl.
| | | |
|---|---|---|
| *G16H 40/20* | (2018.01) |
| *G06T 1/20* | (2006.01) |
| *G06T 7/00* | (2017.01) |
| *G06T 11/00* | (2006.01) |
| *G06T 15/00* | (2011.01) |
| *G16H 50/20* | (2018.01) |
| *G16H 50/80* | (2018.01) |

(52) U.S. Cl.
CPC ............ *G16H 50/80* (2018.01); *G16H 50/20* (2018.01)

(58) Field of Classification Search
CPC ........ G16H 50/00; G16H 50/20; G16H 50/80; G06T 11/001; G06T 15/003; G06T 17/00; G06T 19/00–006; G06T 2219/00; G06T 1/20; G06T 7/00; G06K 7/1413; G06K 19/06028; G06V 20/695; G06V 20/20; G01N 1/02; G01N 21/78; G01N 21/94; G01N 21/80; G01N 21/8483
See application file for complete search history.

(56) References Cited

U.S. PATENT DOCUMENTS

| 11,678,856 B2 * | 6/2023 | Pigott | G01T 7/00 |
| | | | 378/87 |
| 2019/0086296 A1 * | 3/2019 | West | G01N 21/78 |
| 2020/0298240 A1 * | 9/2020 | Oshinski | G01N 1/02 |
| 2021/0042354 A1 * | 2/2021 | Paul | G06F 16/29 |

\* cited by examiner

*Primary Examiner* — Wesner Sajous
(74) *Attorney, Agent, or Firm* — Innovent Law P.C.; Karima F. Gulick

(57) ABSTRACT

A data visualization overlay comprising a facility map including one or more zones; and one or more symbols representing one or more data points wherein the one or more symbols are aggregated in a helical display disposed on the one or more zones thereby allowing a readable representation of the one or more data points on the facility map.

7 Claims, 16 Drawing Sheets

SYSTEM AND METHOD OF TRACKING AND GRAPHICALLY REPRESENTING TEST RESULTS

CROSS-REFERENCE TO RELATED APPLICATIONS

This application claims priority to Provisional Patent Application No. 63/067,845, filed on Aug. 19, 2020, now pending, which is hereby incorporated by reference in its entirety.

BACKGROUND OF THE DISCLOSURE

1. Field of the Disclosure

This disclosure relates generally to a visual representation of test results and a system for tracking and graphically representing contaminants and test results generally. More particularly, the disclosure relates to trending and mapping of progressive data and generating a visual map image to aid in recognizing recurring contamination patterns at given locations, and in nearby or related locations.

2. Description of the Related Art

In markets today, there are very limited products offered for visually representing tracking contaminants over time and space in a facility.

Other products include a series of colored geometric shaped markers representing results surrounding the site location marker on the facility map, however, these solutions are not scalable and not user friendly. In addition, in markets today; there are no products that can provide a sequential, progressive data image for contaminant monitoring sites in the manufacturing facility and/or equipment map that is displayed directly on a map, specifically displaying progressive trend data relative to the order of conforming and non-conforming findings at an individual sampling site, or in nearby or related sites in the process environment.

Other system products offered for environmental results trending and mapping only involve one consolidated trend indicator image on a map for a site, requiring users to open a subsequent folder to see the specific results conformance history for that site. Inability by other products on the market to permit users to easily recognize progressive data trends at nearby or spatially related sites is a problem in the food and consumer products manufacturing industries.

Currently, there are no useful alternatives that effectively assist a food or other consumer products manufacturer to view the results trend history, including conforming and non-conforming results, concurrently and progressively at-a-glance, relative to all sites on the map, to visually display data in a data string that aids the user in recognizing spatial trends relative to a specific sampling site, or between that site and nearby or related sites, relative to a date range selected by the user. As will be disclosed below, the present disclosure addresses these needs and covers a device and method to aid in identifying and recognizing contaminant non-conformance trends, to prevent these inconveniences and solve these issues.

SUMMARY OF THE DISCLOSURE

In one aspect, the present disclosure is embodied as a data visualization overlay which includes a facility map with one or more zones and symbols representing data points where the symbols are aggregated in a helical display disposed on the zones. This allows a readable representation of the e data points on the facility map. In some embodiments, the symbols visually depict a test result, a test data, a contaminant, an organism, a confirming test result, a non-confirming test result, an incidence rate, a dated data point, and/or a test type.

In some embodiments, the symbols comprise a transparent interior so that a plurality of data points are readable. The symbols can be a color-coded polygon, a circle, a star, a rectangle, a crescent, a shape, a circle with a test result number, and/or a solid filled symbol. These symbols can visually depict a test result, a contaminant, and/or a dated data point. In some instances, the symbols are arranged by date and time, where an oldest data point can be either at the center of the helical display or at an outer edge of the helical display and a newest data point is on an opposite end of the helical display from the oldest data point, and vice versa.

In some embodiments, the facility map can be a 2-dimensional map, a 3-dimensional map, an interactive 3-dimensional map, an augmented reality map, and/or a video tour map.

The present disclosure can be embodied as a data visualization overlay system for visually displaying one or more data points. The system includes a facility map with zones, and symbols representing data points and aggregated in a helical display disposed on the zones. This system allows a readable representation of the one or more data points on the facility map.

In some cases, the system also includes testing devices configured to collect a testing data and a testing result, an electronic computing device configured to receive, store and compile the testing data and the testing; and a graphic user interface adapted to display the testing data. The testing result is displayed on the facility map and on the facility map zones. The testing data and the testing result are aggregated by a location and disposed on the facility map and zones. Here, the testing data and the testing results can be color coded and adapted to display a level of contamination, whether a test result is confirming or non-confirming, a type of test conducted or any equivalent and relevant information.

In one embodiment, the system includes a single symbol display at the zones in addition to the helical display. Here a user can toggle between and display both the helical display and the single symbol display when a user clicks on the single symbol display and the helical display. For example, by clicking on the single symbol, the helical display is shown where the user can hover over the symbols within the helical representation and read additional data about each point and each symbol. In other cases, by clicking on each symbol within the helical display, the user can pull up a table with all details of a test conducted at a given area of the facility.

In some embodiment, the symbols in the helical display can include a solid perimeter and a transparent inner side such that multiple shapes can be overlayed to show a plurality of testing data and results over time on the same testing zone area. In other embodiments, the symbols can be a color-coded symbol, a circle, a star, a rectangle, a crescent, a shape, a solid filled symbol, and/or a circle with a test result number or equivalent data depiction.

In one embodiment, the symbols visually depict a test result, a contaminant, an organism, a confirming test result, a non-confirming test result, an incidence rate, and/or a dated data point. In other embodiments, the symbols in the system are arranged by date. Here, for example, an oldest data point can be at the center of the helical display or at an outer edge of the helical display and a newest data point is on an opposite end of the helical display from the oldest data point. The facility map can be a 2-dimensional map, a 3-dimensional map, an interactive 3-dimensional map, an augmented reality map, and/or a video tour map.

In accordance with one form of this disclosure, there is provided a method for analyzing and graphically representing a correlation of a plurality of test results occurring within a physical facility, including a data visualization overlay system implemented on an electronic computing device. The method comprises the steps of receiving a graphical representation of the physical facility including one or more zones; retrieving a data associated with the test results, the data including information on the location of the facility where a test was conducted, a type of test conducted and a time of test conducted; correlating the test results with the graphical representation of the physical facility; and outputting a graphic display showing the data associated with the test results on the graphical representation of the physical facility including one or more symbols representing the data and aggregated in a helical display disposed on the one or more zones.

In some embodiments, the method can also include receiving a user input when a test data is selected and outputting details of the data associated with the test results. In some cases, the outputting of a graphic display shows the data associated with the test results in the helical display and/or a single symbol display. And in other cases, the system can receive a user input to toggle between the helical display and the single symbol display, and displaying data in the helical display and the single symbol display format.

In other embodiments, the method can also include the steps of receiving a master swab site; receiving an image or a video of the facility map; receiving a marking of one or more swab site lists onto the facility map; receiving a data associated with the test results; and outputting a trend report and a visual display of the data associated with the test results.

In other embodiments, the present disclosure is a system and method for tracking contaminants in a manufacturing environment. The system includes one or more testing devices configured to collect testing data and testing results; a computer configured to receive, store and compile testing data and testing results; a graphic user interface adapted to display a map showing testing data and results displayed on an image of a testing facility, where the testing data and results is aggregated by location and color coded to display a level of contamination; and wherein the display of testing data and results are aggregated in a helical display thereby allowing to show multiple testing data and results on a given testing facility map.

In one embodiment, the present disclosure is embodied as a heat map with helical display including one or more shapes with a solid perimeter and a transparent surface such that multiple shapes can be overlayed to show a plurality of testing data and results over time on the same testing zone area.

In one embodiment, the present disclosure is a computerized system for the food, consumer packaged goods, medical device and drug manufacturing industries, where contaminant control from the processing and handling environments is necessary for product safety or quality. More particularly, the disclosure relates to a computer system useful for mapping, tracking and trending microbiological data representing the manufacturing environment.

The FDA Preventive Controls for Human Foods (PCHF) Rule, 21 CFR Part 117, specifically requires food manufacturers to control environmental pathogens in the exposed food product handling environment and equipment where ready-to-eat foods are handled. Verification of effectiveness of sanitation controls for environmental pathogens requires pathogen sampling and testing of the surfaces within the ready-to-eat process environment. The emphasis in the Rule is on control of pathogens or pathogen indicator presence and persistence in the processing environment. Environmental pathogen persistence in the processing environment requires management of data to provide information about pathogen history of recurrence in the manufacturing facility at the same, nearby, or related locations.

High risk produce hydrocooling and packing house environments similarly need control of environmental pathogens, verified through pathogen or pathogen indicator sampling of the environment. The USDA FSIS regulations (9 CFR, Part 430) similarly require Listeria swabbing and analysis on equipment in post lethality exposed product handling and processing surfaces for ready-to-eat meat and poultry. The requirements in other industries for clean room monitoring for the manufacture of medical devices, drugs, etc., conduct microbiological monitoring of the process environment, similarly benefitting from a tool that would help them identify persistence of contaminants and trends for improved control.

The sequence of the colored results markers matches the data relative to sampling dates which were entered into the presently disclosed system. Different colors and/or geometric shapes represent conforming versus non-conforming results. The data markers originate from the site location marker, with the closest data marker to the site locator being the earliest data point in the data string for the date range selected by the user. The last data marker in the user selected date range is located at the end of the progressive data marker string. Different colors and/or shapes are used to discriminate sampling data for individual samples versus composite samples representing multiple sites.

Before explaining the various embodiments of the disclosure in detail, it is to be understood that the disclosure is not limited in its application to the details of construction and to the arrangements of the components set forth in the following description or illustrated in the drawings. Rather, the disclosure is capable of other embodiments and of being practiced and carried out in various ways. Also, it is to be understood that the terminology employed herein is for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the disclosure of the application, which is measured by the claims, nor is it intended to be limiting as to the scope of the disclosure in any way.

For a better understanding of the disclosure, its operating advantages and the specific objects attained by its uses, reference should be made to the accompanying drawings and descriptive matter in which there are illustrated preferred embodiments of the disclosure.

Various objects, features, aspects and advantages of the present embodiment will become more apparent from the following detailed description of embodiments of the embodiment, along with the accompanying drawings in which like numerals represent like components.

BRIEF DESCRIPTION OF THE DRAWINGS

It should be noted that the drawing figures may be in simplified form and might not be to precise scale.

FIG. 15 is a Graphical User Interface showing the system according to one embodiment of the present disclosure with a setup page.

FIG. 16 is another Graphical User Interface showing the system according to another embodiment of the present disclosure with a parameter setup page.

The same elements or parts throughout the figures of the drawings are designated by the same reference characters, while equivalent elements bear a prime designation.

DETAILED DESCRIPTION OF THE DISCLOSURE

The embodiment and various embodiments can now be better understood by turning to the following detailed description of the embodiments, which are presented as illustrated examples of the embodiment defined in the claims. It is expressly understood that the embodiment as defined by the claims may be broader than the illustrated embodiments described below. Many alterations and modifications may be made by those having ordinary skill in the art without departing from the spirit and scope of the embodiments.

Figure 1:
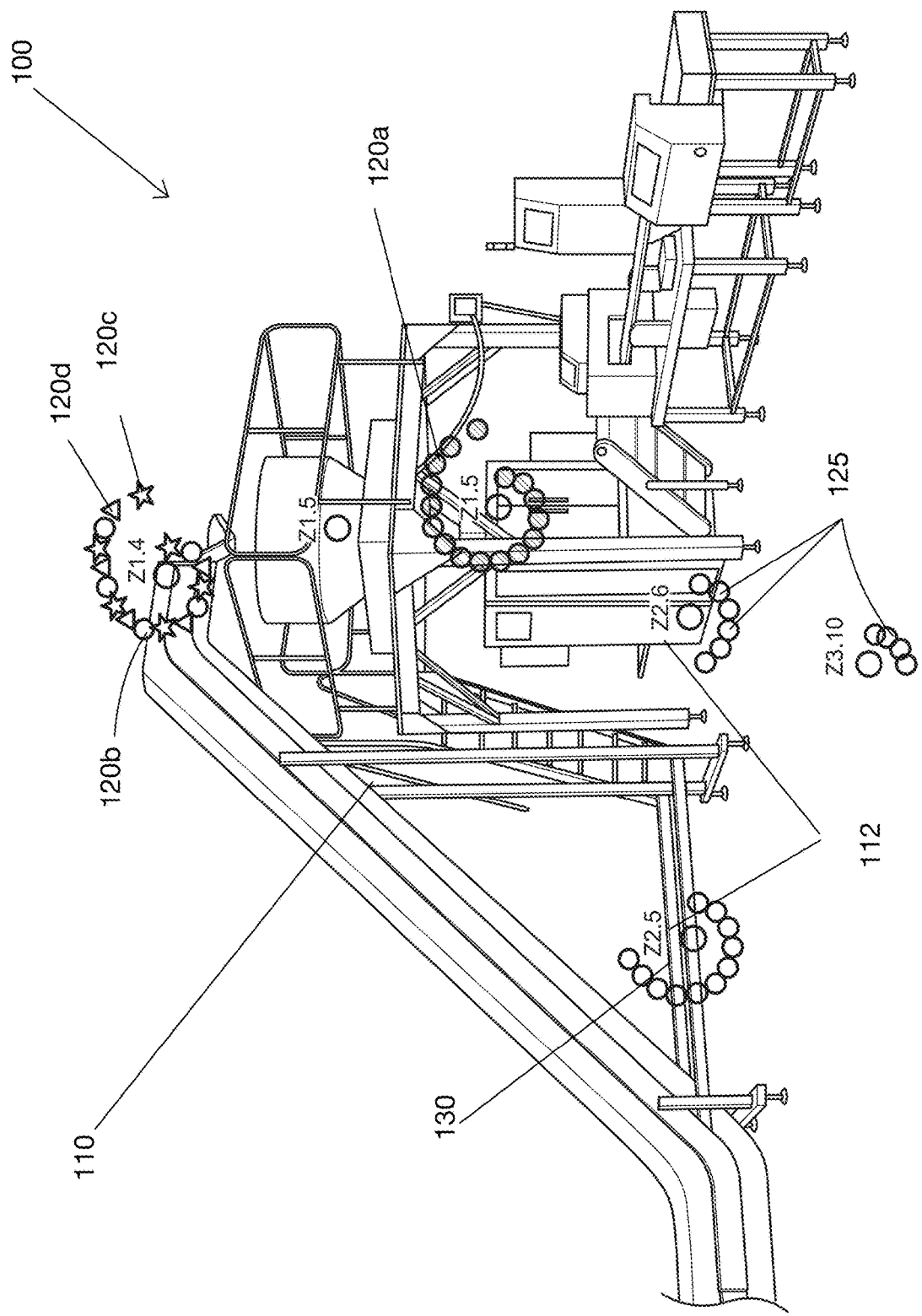
FIG. 1 is a display view of one embodiment of the present disclosure showing a data visualization overlay and heat map in a facility.
Figure 4:
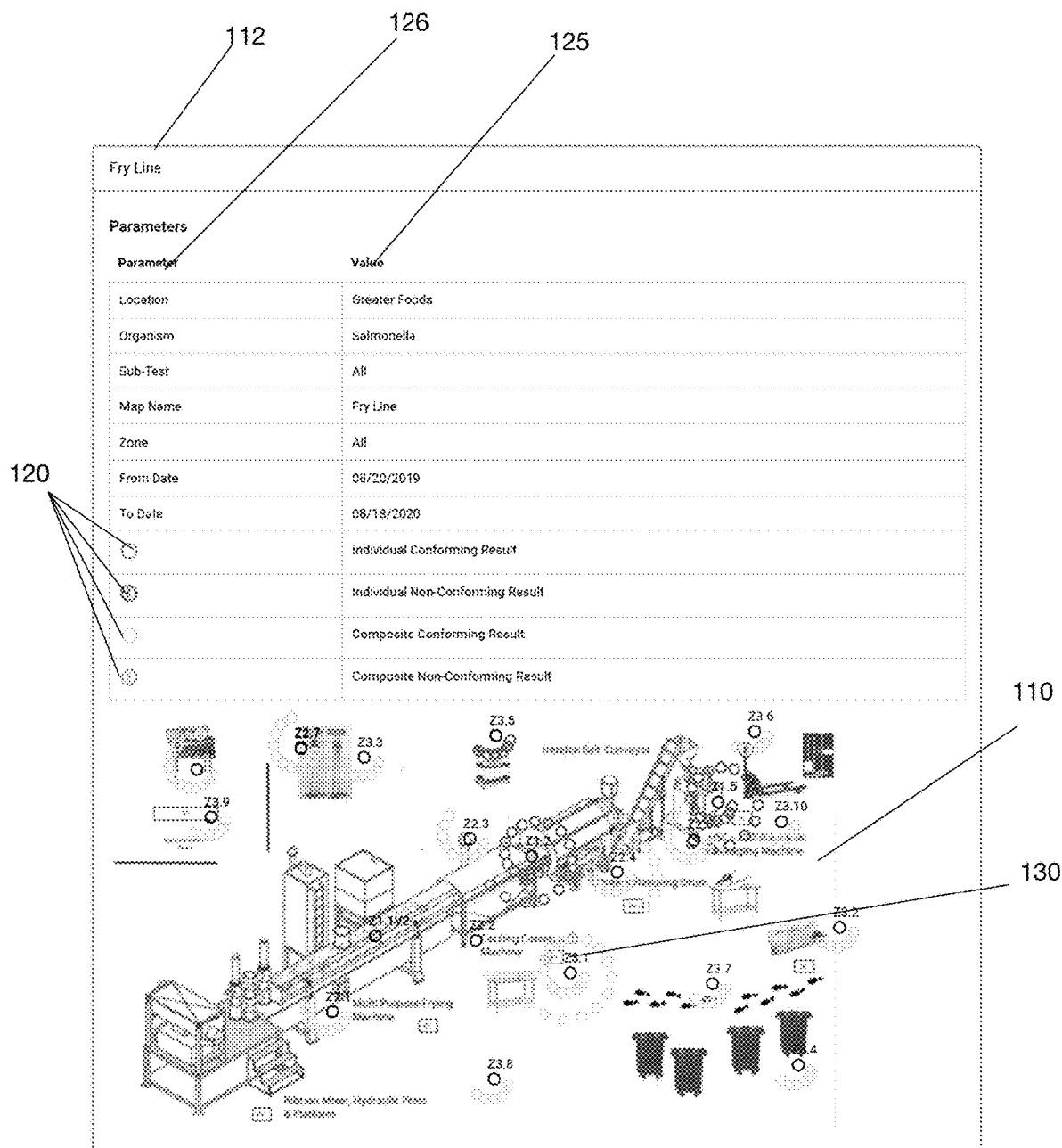
FIG. 4 is a display view of one embodiment of the present disclosure showing a heat map in a facility according to user parameters.

Referring now to the drawings and the characters of reference marked thereon, FIG.1 a data visualization overlay 100 which includes a facility map 110 with one or more zones 112 and symbols 120 representing data points where the symbols are aggregated in a helical display 130 disposed on the zones. This allows a readable representation of the data points on the facility map. In some embodiments, the symbols visually depict a test result, a test data, a contaminant, an organism, a confirming test result, a non-confirming test result, an incidence rate, a dated data point, and/or a test type as shown in FIG. 4

Figure 2:
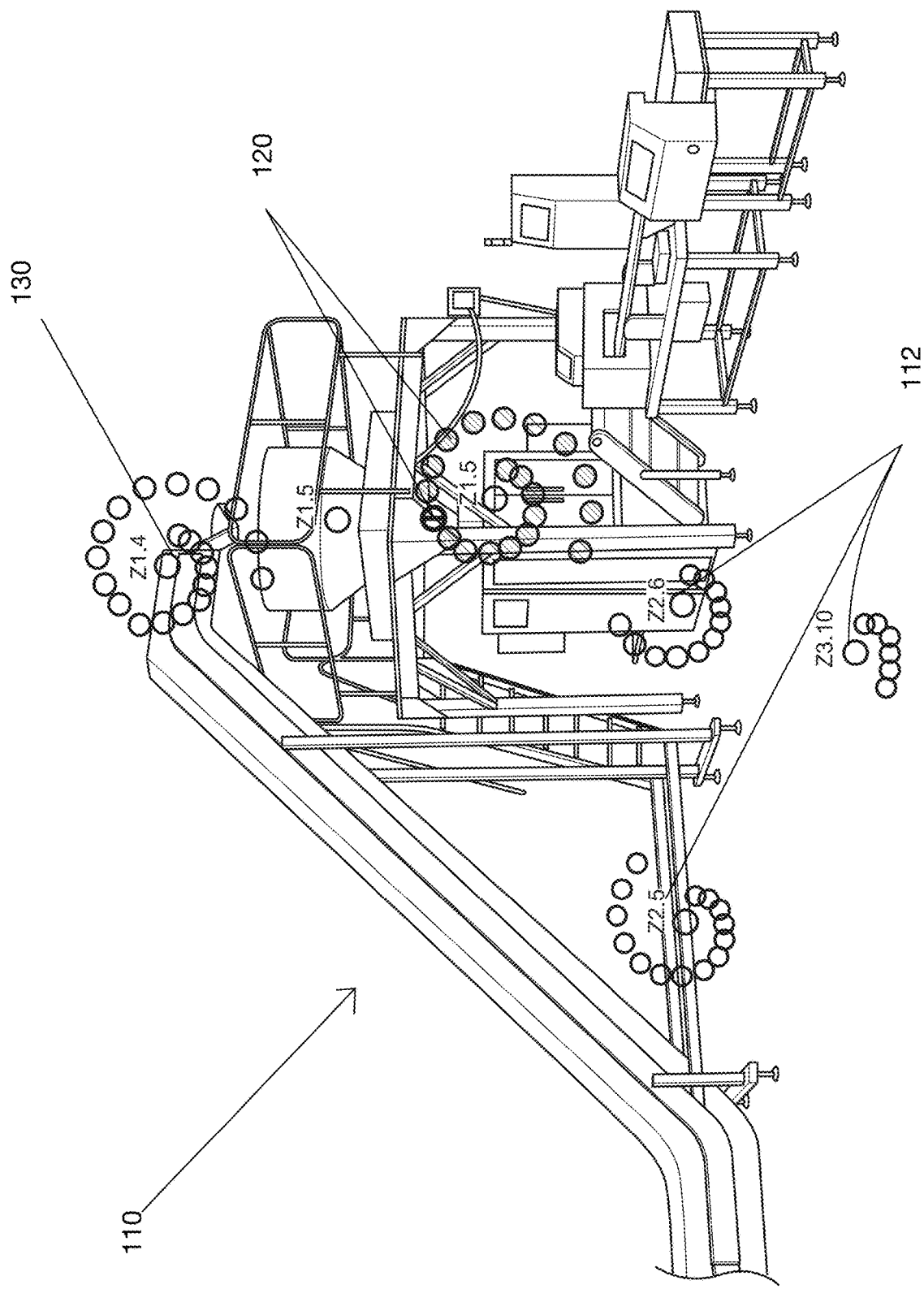
FIG. 2 is a schematic view of a heat map showing contaminant tracking over time and space.
Figure 3:
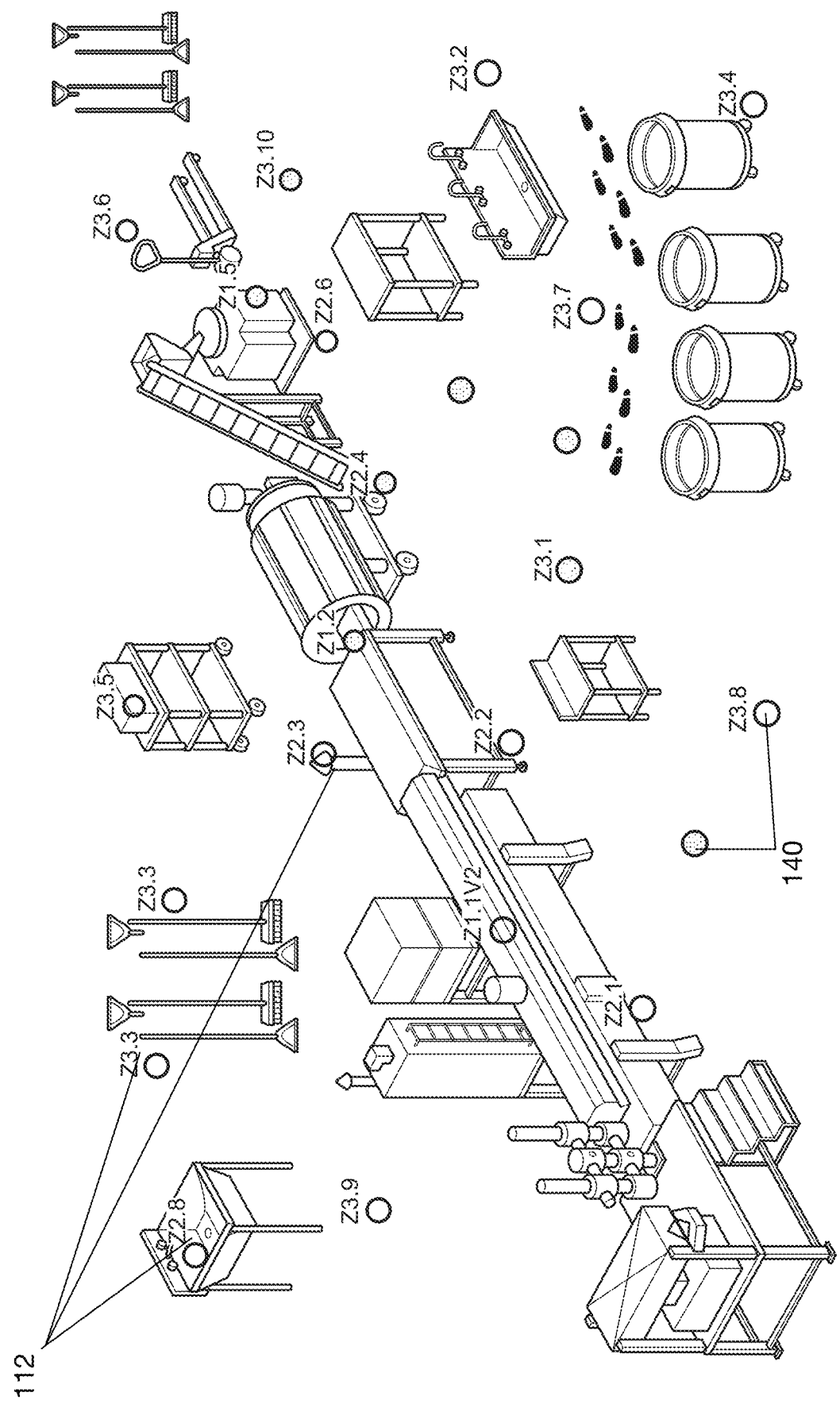
FIG. 3 is a display view of yet another embodiment of the present disclosure showing a heat map in a facility.
Figure 5:
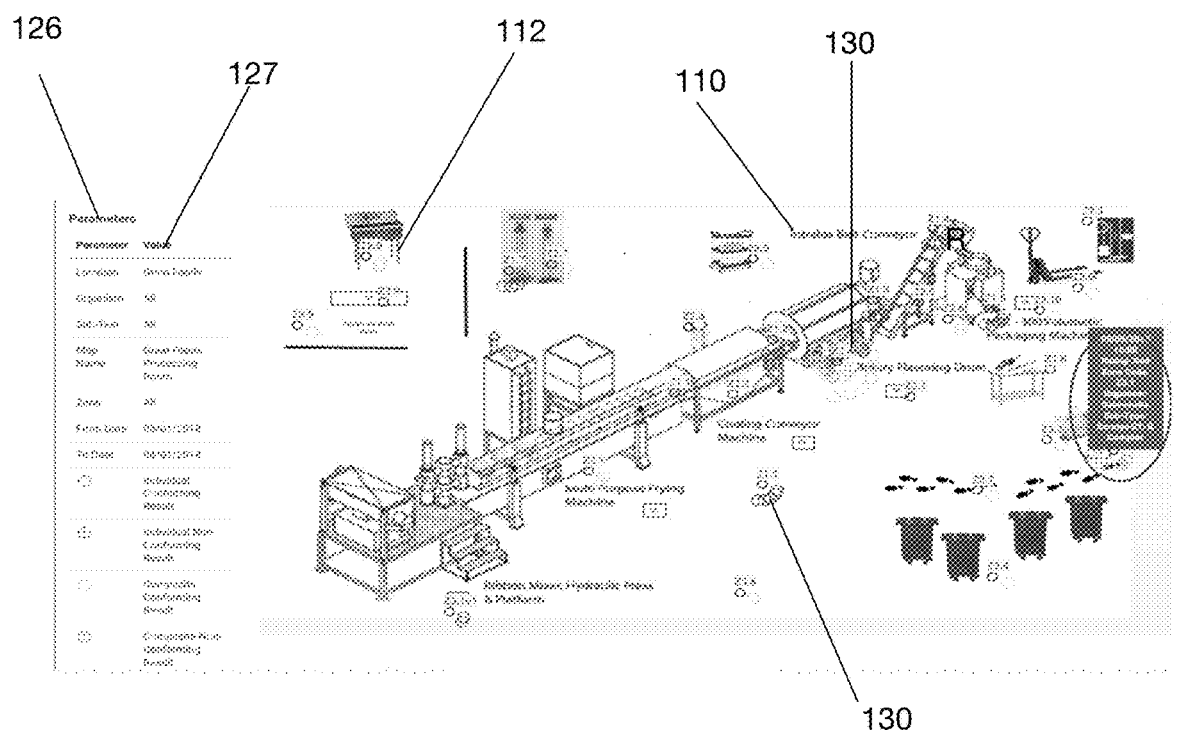
FIG. 5 is a display view of one embodiment of the present disclosure showing a heat map in a facility according to user parameters and user set values.

In FIG. 2 Zone 2.5, the symbols comprise a transparent interior 121 so that a plurality of data points are readable. The symbols can be a color-coded polygon 120a, a circle 120b, a star 120c, a rectangle, a crescent, a shape, a triangle 120d, a circle with a test result number, and/or a solid filled symbol. These symbols can visually depict a test result, a contaminant, and/or a dated data point as shown in FIG. 4 and FIG. 5.

Figure 8:
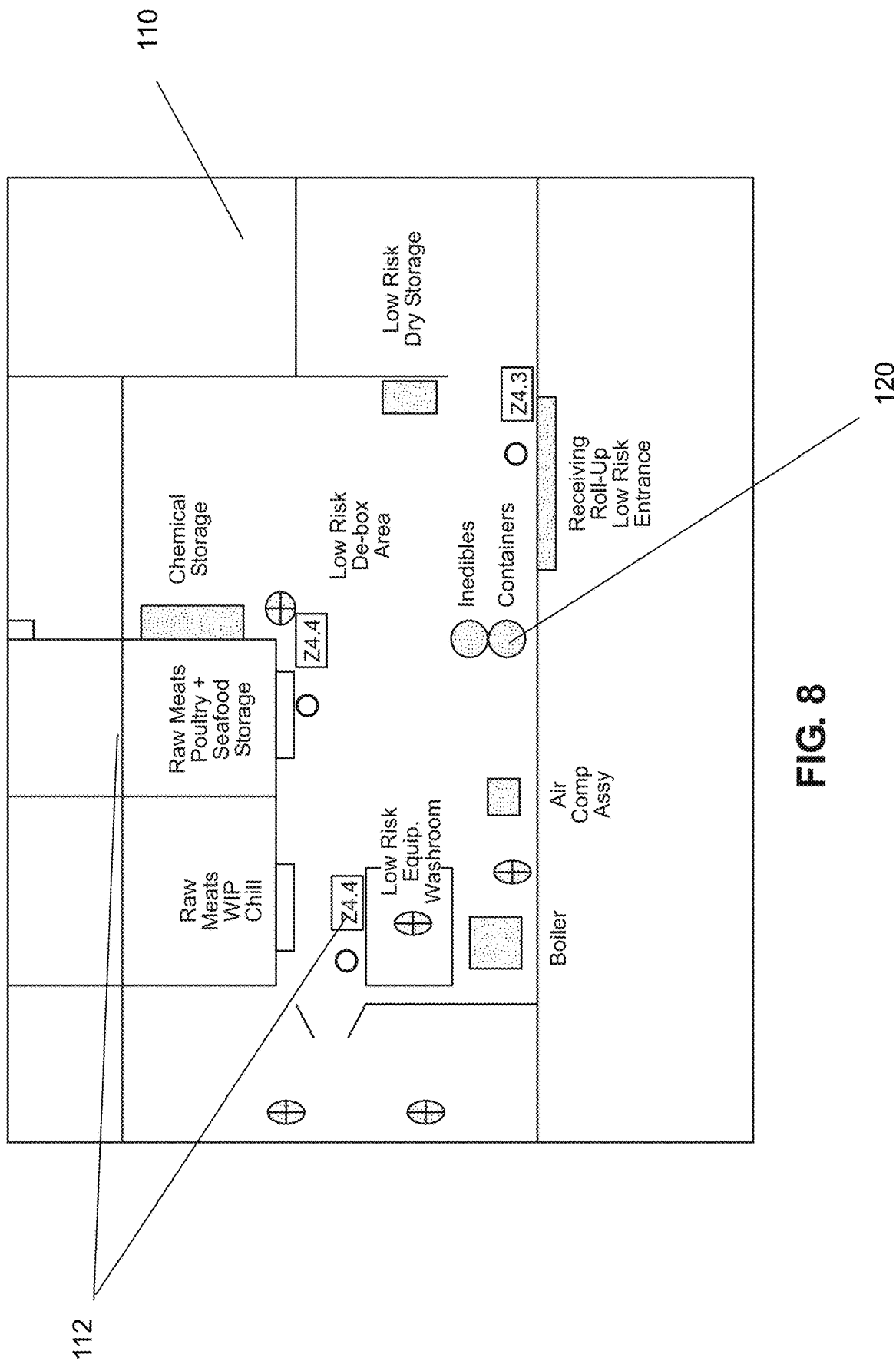
FIG. 8 is a display view of another embodiment of the present disclosure showing a visual data representation in a facility.
Figure 9:
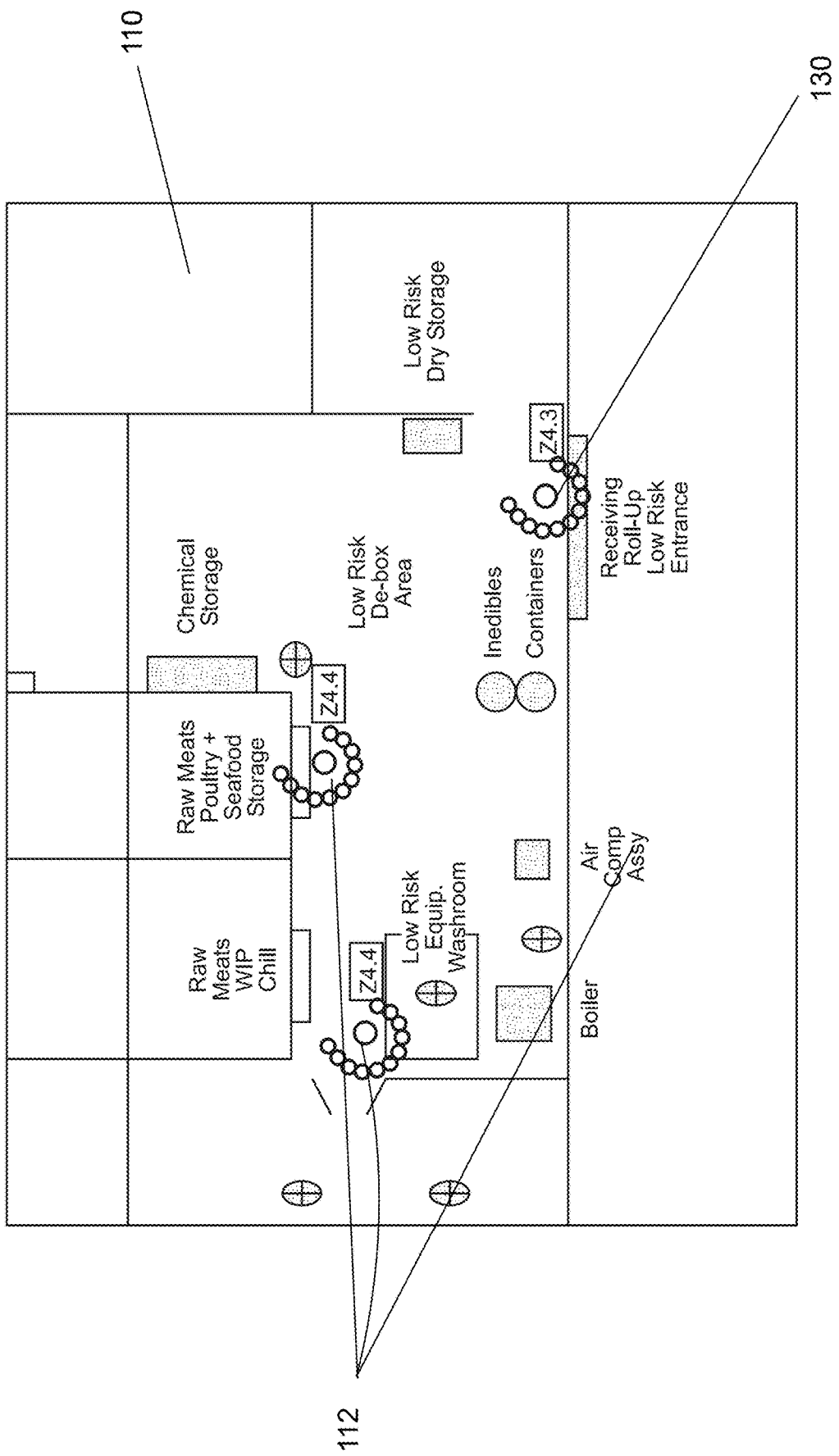
FIG. 9 is a display view of yet another embodiment of the present disclosure showing a visual data representation in a facility.

In some instances, as shown in FIG. 2, the symbols are arranged by date and time, where an oldest data point can be either at the center of the helical display or at an outer edge of the helical display and a newest data point is on an opposite end of the helical display from the oldest data point, and vice versa. In some embodiments, the facility map can be a 2-dimensional map as shown in FIGS. 8 and 9, a 3-dimensional map as shown in FIGS. 1 through 5, an interactive 3-dimensional map, an augmented reality map, and/or a video tour map (not depicted in the drawings).

Figure 12:
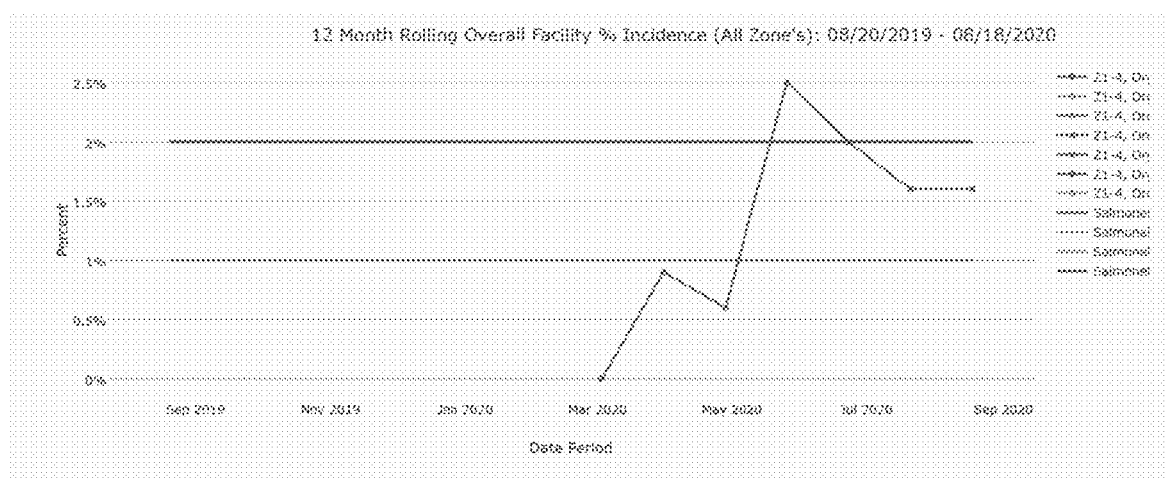
FIG. 12 is a graphical representation of another embodiment of the present disclosure showing a 12-month rolling overall facility percent incidence in various physical zones.
Figure 13:
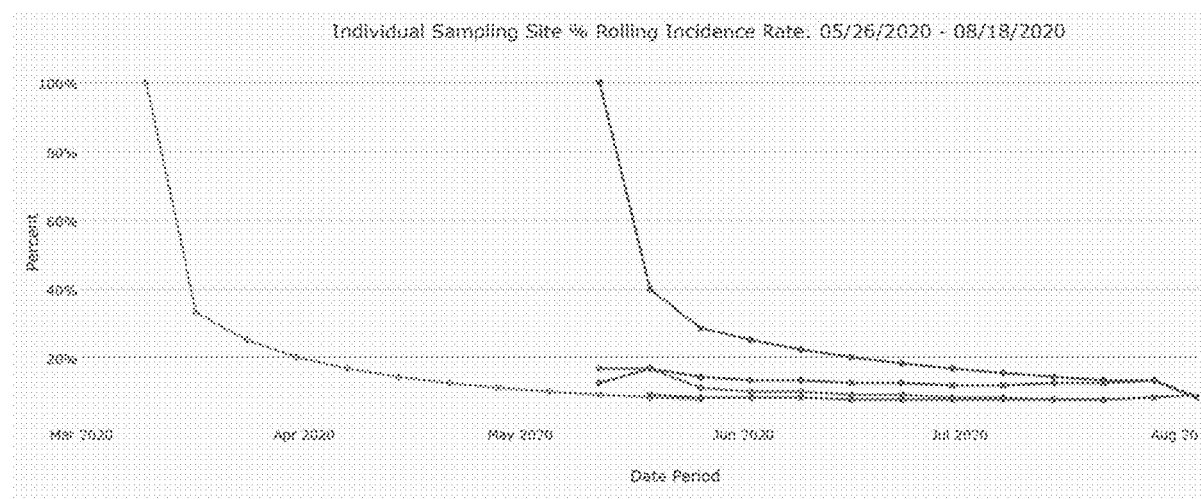
FIG. 13 is a graphical representation of another embodiment of the present disclosure showing a percentage incidence by individual testing sites over a period of time.
Figure 14:
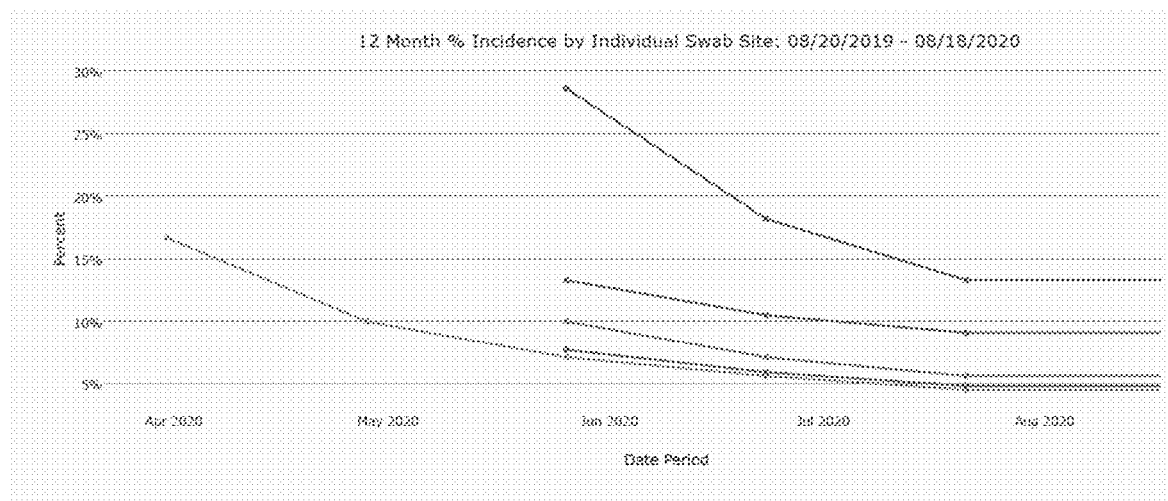
FIG. 14 is a graphical representation of another embodiment of the present disclosure showing a 12-month percent incidence by Individual swab sites.
Figure 15:
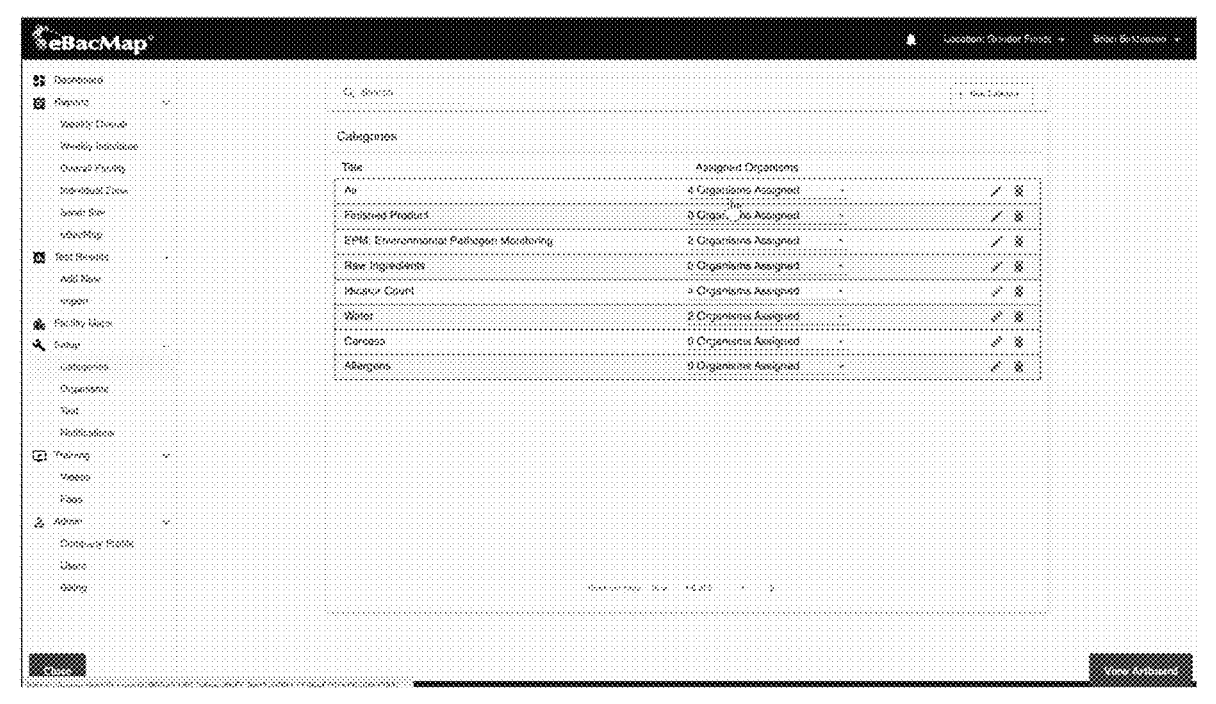
Figure 16:
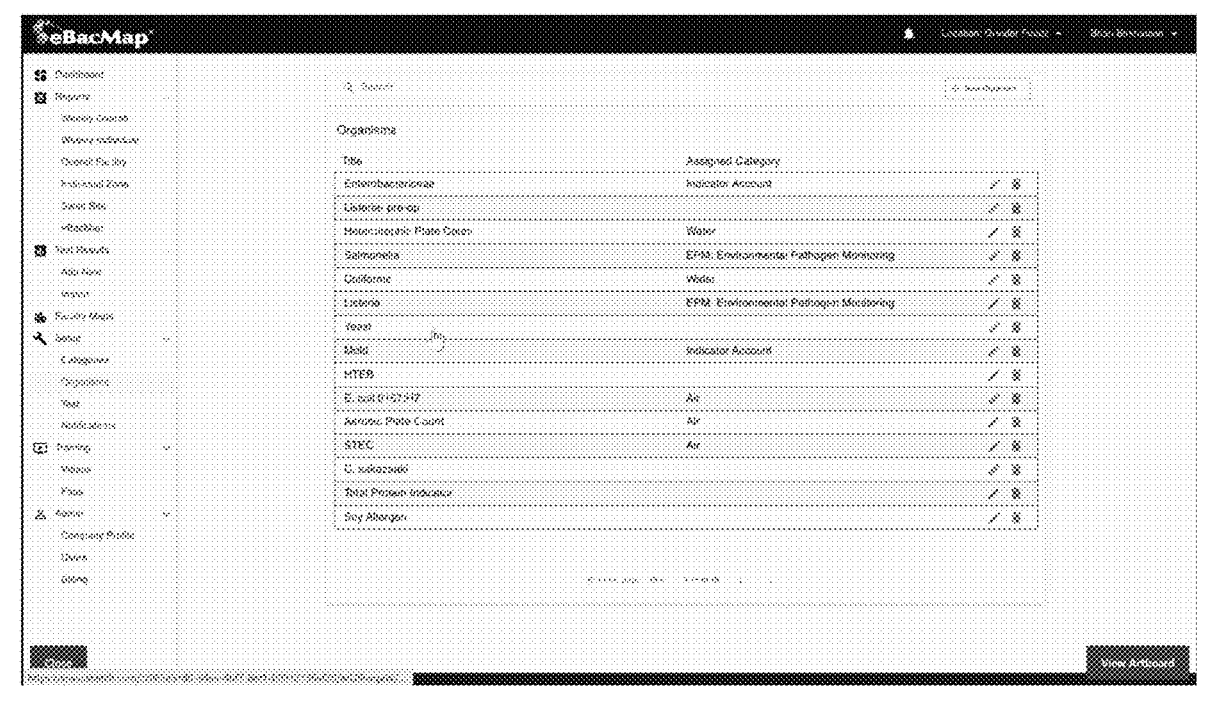

The present disclosure can be embodied as a data visualization overlay system for visually displaying one or more data points. The system includes a facility map with zones, and symbols representing data points and aggregated in a helical display disposed on the zones. This system allows a readable representation of the one or more data points on the facility map. Here, the system analyzes testing data and allows for a user friendly reading of these results on the overlays and graphical representations 100. FIGS. 12 through 14 show compiled test results along with trailing percent rate incidence by individual swab and test sites. These compilations can be aggregated from the heat map and overlay or can be depicted on the overlay In some cases as shown in FIGS. 4, 5,15 and 16 , the system also includes testing devices configured to collect a testing data and a testing result, an electronic computing device configured to receive, store and compile the testing data and the testing; and a graphic user interface adapted to display the testing data. The testing result is displayed on the facility map and on the facility map zones. The testing data and the testing result are aggregated by a location and disposed on the facility map and zones. Here, the testing data and the testing results can be color coded and adapted to display a level of contamination, whether a test result is confirming or non-confirming, a type of test conducted or any equivalent and relevant information.

Figure 6:
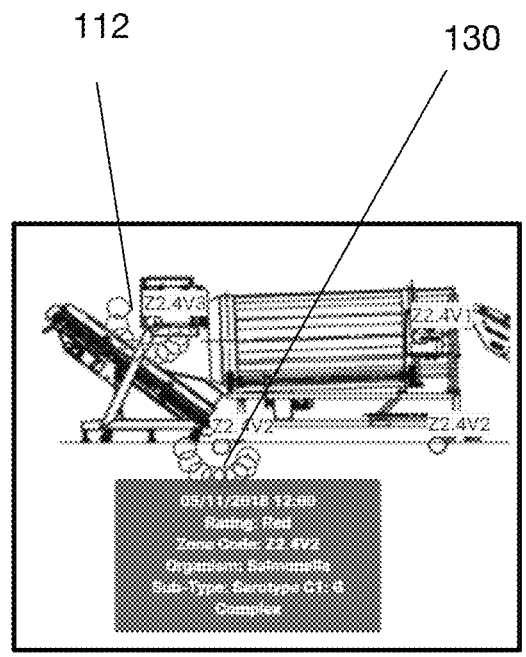
FIG. 6 shows a zone data visualization overlay.

In one embodiment, the system includes a single symbol display at the zones in addition to the helical display 130. Here a user can toggle between and display both the helical display 130 and the single symbol display 140 when a user clicks on the single symbol display and the helical display. For example, by clicking on the single symbol 140, the helical display 130 is shown where the user can hover over the symbols within the helical representation and read additional data about each point and each symbol as shown in FIGS. 4 and 6. In other cases, by clicking on each symbol within the helical display, the user can pull up a table with all details of a test conducted at a given area of the facility. The single symbol display 140 can include a number of occurrences of contamination or other relevant test result as a number on the symbol or dot.

Figure 7:
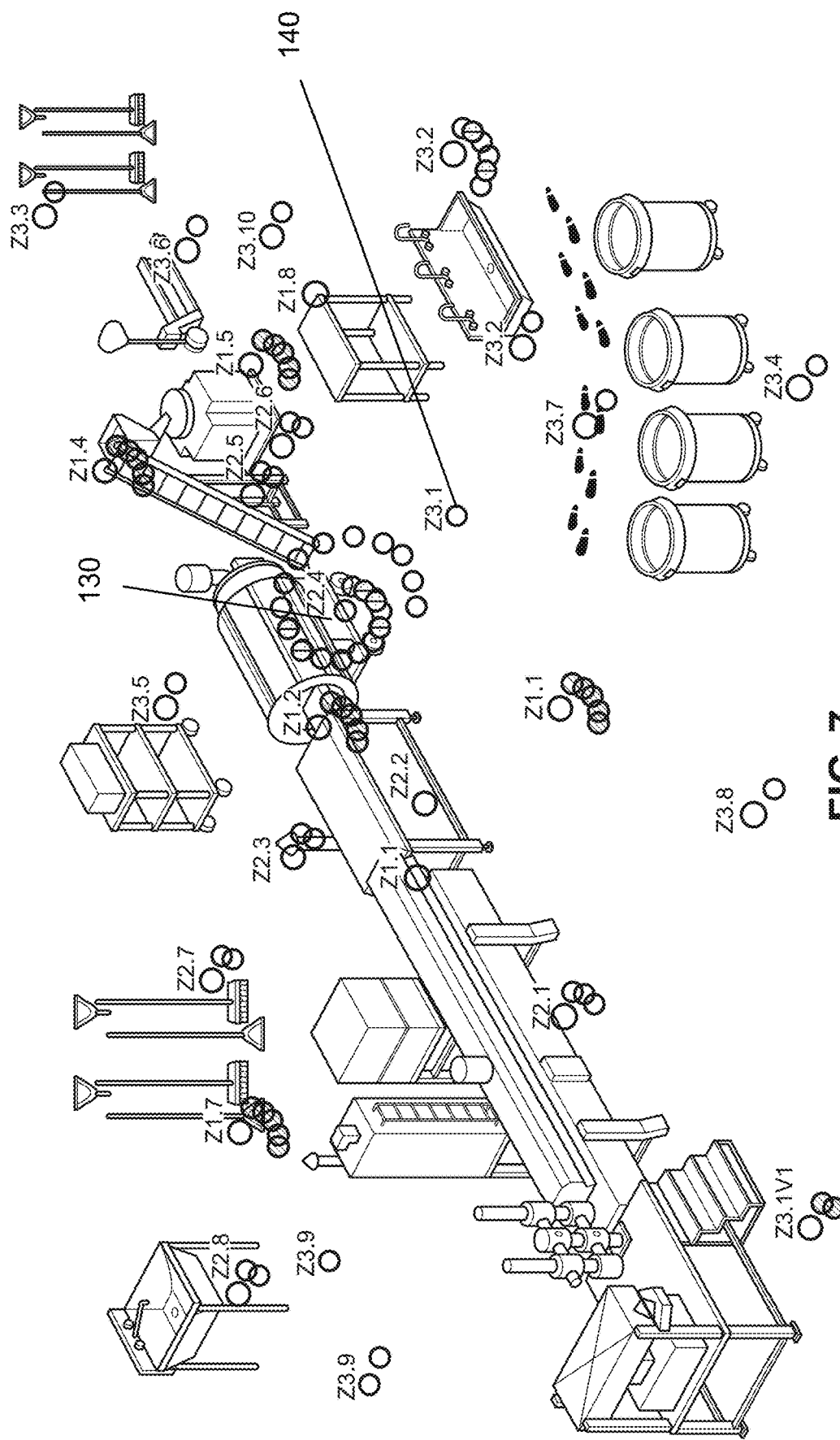
FIG. 7 is a display view of one embodiment of the present disclosure showing a visual data representation in a facility.

FIGS. 1 and 7 show the symbols in the helical display 140, which can include a solid perimeter and a transparent inner side such that multiple shapes can be overlayed to show a plurality of testing data and results over time on the same testing zone area. The symbols can be a color-coded symbol, a circle, a star, a rectangle, a crescent, a shape, a solid filled symbol, and/or a circle with a test result number or equivalent data depiction. Here, each symbol may depict a different test, contaminant tested, organism tested and confirmed etc.

FIG. 7 the symbols visually depict a test result, a contaminant, an organism, a confirming test result, a non-confirming test result, an incidence rate, and/or a dated data point. In other embodiments, the symbols in the system are arranged by date. Here, for example, an oldest data point can be at the center of the helical display or at an outer edge of the helical display and a newest data point is on an opposite end of the helical display from the oldest data point. The facility map can be a 2-dimensional map, a 3-dimensional map, an interactive 3-dimensional map, an augmented reality map, and/or a video tour map.

Figure 10:
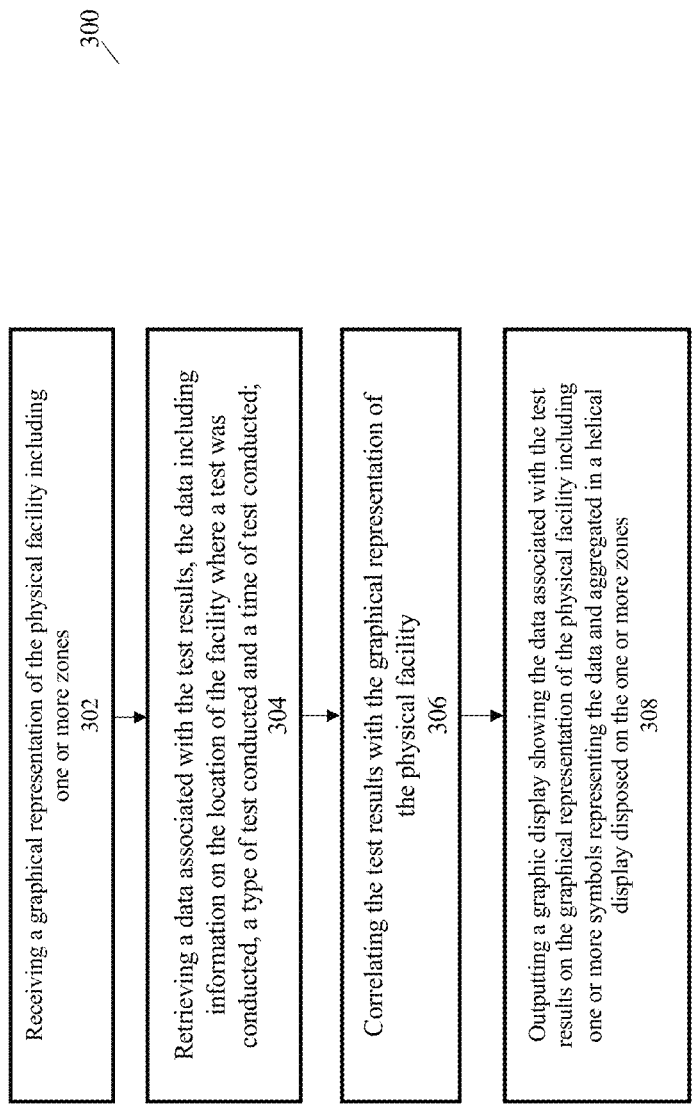
FIG. 10 is a flowchart showing a method according to one embodiment of the present disclosure.
Figure 11:
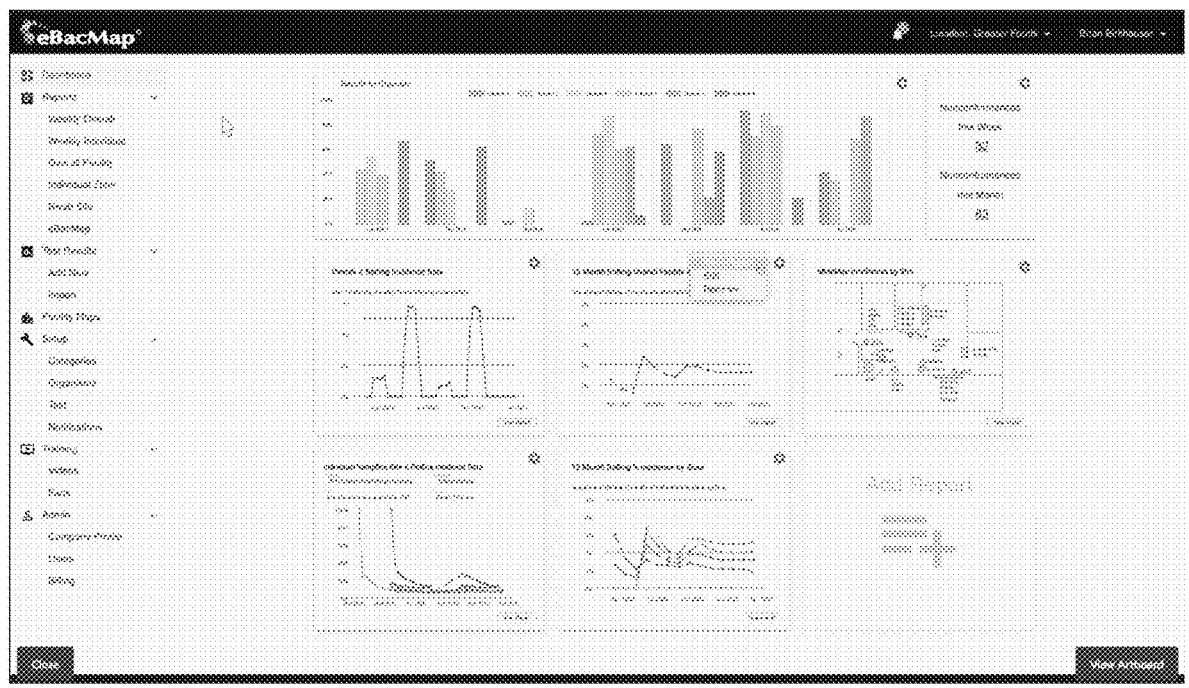
FIG. 11 is a Graphical User Interface showing the system according to one embodiment of the present disclosure.

FIG. 10 shows a method 300 for analyzing and graphically representing a correlation of a plurality of test results occurring within a physical facility, including a data visualization overlay system implemented on an electronic computing device. The method comprises the steps of receiving a graphical representation of the physical facility including one or more zones 302; retrieving a data associated with the test results, the data including information on the location of the facility where a test was conducted, a type of test conducted and a time of test conducted 304; correlating the test results with the graphical representation of the physical facility 306; and step 308 outputting a graphic display showing the data associated with the test results on the graphical representation of the physical facility including one or more symbols representing the data and aggregated in a helical display disposed on the one or more zones.

In some embodiments, the method can also include receiving a user input when a test data is selected and outputting details of the data associated with the test results. In some cases, the outputting of a graphic display shows the data associated with the test results in the helical display and/or a single symbol display. And in other cases, the system can receive a user input to toggle between the helical display and the single symbol display, and displaying data in the helical display and the single symbol display format.

In other embodiments, the method can also include the steps of receiving a master swab site; receiving an image or a video of the facility map; receiving a marking of one or more swab site lists onto the facility map; receiving a data associated with the test results; and outputting a trend report and a visual display of the data associated with the test results.

In other embodiments, the present disclosure is a system and method for tracking contaminants in a manufacturing environment. The system includes one or more testing devices configured to collect testing data and testing results; a computer configured to receive, store and compile testing data and testing results; a graphic user interface adapted to display a map showing testing data and results displayed on an image of a testing facility, where the testing data and results is aggregated by location and color coded to display a level of contamination; and wherein the display of testing data and results are aggregated in a helical display thereby allowing to show multiple testing data and results on a given testing facility map.

In one embodiment, the present disclosure is embodied as a heat map with helical display including one or more shapes with a solid perimeter and a transparent surface such that multiple shapes can be overlayed to show a plurality of testing data and results over time on the same testing zone area.

In one embodiment, the present disclosure is a computerized system for the food, consumer packaged goods, medical device and drug manufacturing industries, where contaminant control from the processing and handling environments is necessary for product safety or quality. More particularly, the disclosure relates to a computer system useful for mapping, tracking and trending microbiological data representing the manufacturing environment.

FIG. 7 shows a system for tracking contaminants in a manufacturing environment comprising: one or more testing devices configured to collect testing data and testing results; a computer configured to receive, store and compile testing data and testing results; a graphic user interface adapted to display a map showing testing data and results displayed on an image of a testing facility 110, wherein the testing data and results is aggregated by location and color coded to display a level of contamination 120; and wherein the display of testing data and results are aggregated in a helical display 130 thereby allowing to show multiple testing data and results on a given testing facility map.

In one embodiment, the heat map 100 has a helical display 130 which includes one or more shapes with a solid perimeter and a transparent surface such that multiple shapes can be overlayed to show a plurality of testing data and results over time on the same testing zone area.

In one aspect, the present disclosure is embodied as a system with web-based system as a service tool for manufacturers to utilize their microbiological data representing the manufacturing process, equipment and handling environment to recognize data trends relative to contaminant location, frequency, and patterns.

In one embodiment, the present disclosure is a computer system into which the user enters their environmental test results representing the process environment and equipment and the date of sampling. The user enters images such as facility maps 110 into the system 200 of the manufacturing facility representing equipment, processing rooms, zones 112 and/or processing lines or areas. The user enters their sampling site descriptions and locates those on their facility images. The system uses the facility images and generates a report known as an eBacMap consisting of the facility or equipment image with monitoring sites located and progressive results trend history on it.

The progressive results trend history report discriminates conforming from non-conforming contaminant results representing the site by different colors, sequentially and progressively over the date range selected by the user. The progressive contaminant results trend imagery at sample site locations on maps is generated by the system. The trend maps provide a visual aid that to help the user more readily identify non-conformance problems at a single site, and also patterns with non-conformances at nearby or related sites in the environment. All data mapping, tracking and trending is relative to the user selected sampling sites, user monitoring program and test results, user defined test types and acceptance criteria, and the date range for the reports as selected by the user. The system has a dashboard feature with default percent incidence reports for individual sampling sites, the overall facility, and by specific hygiene zone.

In an alternative embodiment, the various elements of the eBacMap or present disclosure's data mapping, tracking and trending system program include a drop-down bar functions for data mapping, tracking, and trending reports called the 'Dashboard'. The user results entry is performed in the 'Enter Results' drop-down bar function. Facility maps on which results tracking, trending and mapping are entered in the 'Facility Maps' drop-down function menu. Sampling sites entry for system mapping, tracking and trending data are entered in the 'Swabs' drop-down bar function. Sites entered into the 'Swabs' 'Sites' list are located on the 'Facility Maps' for tracking and trending data to display.

The system of the present disclosure may include a 'Dashboard' for all of the data mapping, tracking and trending outputs from the system, including weekly, monthly and ad-hoc reports. The system includes 'Setup' drop-down bar functions for defining system users, system administrators, and defining persons to be notified with data trends. Persons can receive notifications for individual results non-conformances and/or trend non-conformances. The user defines the incidence trend action limits.

In some embodiments, the 'Setup' functions can also include defining 'Categories' of data to be mapped, tracked and trended, such as Environmental Pathogen Monitoring, Air, Water, Finished Product, or others defined by the user. Within each 'Category' the 'Organisms' to be mapped, tracked and trended are defined, and for each 'Organisms' type the specific 'Tests' that are trended defined.

In one embodiment, the present disclosure is embodiment as a system and method where a testing is done by means of swab, scraping, pipette, food residue testing, air testing or any other contaminant testing method. The results of the testing are then imported into a computer system. Various testing data and data results are imported into the system of the present disclosure.

The results are then codified and displayed by zone, subzone and shown on a heat map. The heat map is defined as a map of a facility with various testing locations where the results are graphically overlayed on the heat map. Results are also codified by contact surface etc.

When a user hovers on the graphical representation of the testing results, various data is shown. The user can also filter specific parameters and test results to be shown on the map when the result representation is hovered. In one embodiment, the test result is a circle with a colored perimeter to indicate the level of safety and/or contamination, and the inner surface of the circle is transparent thereby allowing overlaying of multiple results over time and space while still being visible and readily readable by a user.

In one embodiment, the user can hover on the circle with color, and get date of the testing, and exact location, (locations can also be divided into sublocations and vector sites, subsample of a smaller portion) and the user can select which contaminant testing to view.

In one embodiment, the trend graphs are viewed through a dashboard. In other embodiments, the trend graphs can be viewed directly on the heat map. In one embodiment, the graphical representation of the testing results on the heat map is shown as one or various shapes of various codified colors in a helical way.

This representation allows for more progressive data, and a user can look at one site and see history of the location by looking at the data trend nearby. In another embodiment, the helical representation of the results is such that the oldest tests are at the center of the helix while the newest results are displayed at the outer edges of the helical representation.

In one embodiment, the data visualization overlay 100 includes a live feed of live results, and the results are added to the facility map live as they are being received by the system. In other embodiments, the user may select a date range to display the data visualization overlay by. In some cases, the results can be filtered and displayed by types of organisms, contaminants or tests.

In another embodiment, the present disclosure is a heat map showing where contaminant issues arise over time and space. Once a user gets a reading of pathogens, the system displays the codified testing result on the heat map. Results can be shown over a long period of time. In some embodiments, the user can upload a blue print of their food processing system or facility. Results are displayed on the graphical and geographical representation of the uploaded facility map.

In one embodiment, each test is marked with a circle. Color is used to indicate positivity or negativity of a contaminant test. In a particular embodiment, the results are shown in spiral of colored shapes to show trend of contaminant testing and tracking over time.

In a particular embodiment, the system 200 includes drop-down bar functions for data mapping, tracking, and trending reports called the 'Dashboard'. The system may also include a 'Setup' drop-down bar functions for defining system users, system administrators, and defining persons to be notified with data trends. Users can receive notifications for individual results non-conformances and/or trend non-conformances. The user defines the incidence trend action limits. The 'Setup' functions can additionally include defining 'Categories' of data to be mapped, tracked and trended, such as Environmental Pathogen Monitoring, Air, Water, Finished Product, or others defined by the user. Within each 'Category' the 'Organisms' to be mapped, tracked and trended are defined, and for each 'Organisms' type the specific 'Tests' that are trended defined.

The system 200 may also include in the 'Setup' menu the admin, 'Categories' for mapping, tracking and trending in the system. Here, the user can identify and name the 'categories'. Typical 'categories might include 'EPM: Environmental Pathogen Monitoring', 'Water', 'Air', 'Indicator Count', 'Finished Product', 'Raw Ingredients', etc. In the 'Setup' menu the admin user adds the 'Organisms' for each of the 'Categories' for mapping, tracking and trending in the system. The category of 'Organisms' is custom named by the admin user. In one example the 'Organisms' added by the user for mapping, tracking and trending are 'Listeria', 'Salmonella', 'Enterobacteriaceae', 'Yeast', 'Mold', and 'Coliforms'. In the 'Setup' menu the admin user adds 'Tests' for mapping, tracking and trending in the system for each 'Organism'. In the example below the 'Organism' in the 'EPM: Environmental Pathogen Monitoring' 'Category' will map, track and trend the 'Listeria' 'Organism', including both the Listeria 'monocytogenes' and 'like' 'Sub Tests'. In the 'Setup' menu the admin user adds email 'Notifications' for mapping, tracking and trending in the system. The admin user selects email addresses for every person who will receive 'Result Entry Notifications'. A 'Result Entry Notification' is an email notification to specified notification recipients, for an individual non-conformance that is recognized when the 'user' enters individual results. The admin user selects the 'Category' and the 'Organisms' for which each notification recipient to receive notification for 'Any Positive/Non-Conforming', or can 'Disable' 'Organisms Notifications'.

In one embodiment, the system 2 includes 'Notifications' for persons to receive mapping, tracking and trending alerts from the system for 'Overall Facility % Incidence Rate' in the 'Category', for an 'Overall % Incidence-4-week' period. The user sets an 'Organism Notification' with a '% Incidence Limit' for aggregate data trend non-conformances above the user selected '% Incidence Limit'. The admin user can alternatively 'Disable' the trend notifications. The user can add email 'Notifications' for persons to receive mapping, tracking and trending alerts from the system for 'Overall Facility % Incidence Rate' in the 'Category', for an 'Overall % Incidence-12-Month' period. The user sets an 'Organism Notification' with a '% Incidence Limit' for aggregate data trend non-conformances above the user selected '% Incidence Limit'. The admin user can alternatively 'Disable' the trend notifications. In other embodiments, mapping, tracking and trending alerts from the system 200 can be set and reported for 'Individual Site % Incidence Rate' in the 'Category', for a 'Site % Incidence-12 Month' trend period. The user sets an 'Organism Notification' with a '% Incidence Limit' for aggregate data trend non-conformances above the user selected '% Incidence Limit'. The admin user can alternatively 'Disable' the trend notifications.

In one embodiment of the system 200, a master swab site list can be created. Here, a user can enter sampling site information for each location for which data will be input, within sanitary zones 1, 2, 3, and 4, into the 'swabs', 'sites' entry area of the system. Any type of sample can be entered, including swab surfaces, product residue or scrapings from surfaces, air, water, or in-process food samples. Users can enter the site number and a vector site number, if applicable. The user selects whether the site represents a composite of surfaces, documents a narrative description of the sample, and can elect to upload a diagram or photograph image with the sampling surface indicated. Image files such as 'gif, jpeg' can be used. The images can be dragged and dropped into the System Site. The user then selects to enable the site so it can be included in the trend reports.

As mentioned above, other embodiments and configurations may be devised without departing from the spirit of the invention and the scope of the appended claims.

The invention claimed is:

1. A data visualization overlay system for visually displaying one or more data points comprising:
   a) a facility map including one or more zones; and
   b) one or more symbols representing one or more data points and aggregated in a helical display disposed on the one or more zones thereby allowing a readable representation of the one or more data points on the facility map; wherein
   the one or more symbols arranged in the helical display include a solid perimeter and a transparent inner side such that multiple shapes can be overlayed to show a plurality of testing data and results over time on a same testing zone area.

2. The data visualization overlay system of claim 1 further including:
   a) one or more testing devices configured to collect a testing data and a testing result;
   b) an electronic computing device configured to receive, store and compile the testing data and the testing; and
   c) a graphic user interface adapted to display the testing data and the testing result on the facility map and on the one or more zones, wherein at least one of the testing data and the testing result is aggregated by a location and disposed on the facility map and on the one or more zones, and wherein the testing data and the testing result is color coded and adapted to display a level of contamination.

3. The data visualization overlay system of claim 2 further including a single symbol display at the one or more zone wherein the graphic user interface includes a toggle function adapted to toggle between and display both the helical display and the single symbol display when a user clicks on the single symbol display and the helical display.

4. The data visualization overlay system of claim 1 wherein the one or more symbols are at least one of a color-coded symbol, a circle, a star, a rectangle, a crescent, a shape, a solid filled symbol, and a circle with a test result number.

5. The data visualization overlay system of claim 1 wherein the one or more symbols visually depicts at least one of a test result, a contaminant, an organism, a confirming test result, a non-confirming test result, an incidence rate, and a dated data point.

6. The data visualization overlay system of claim 1 wherein the one or more symbols are arranged by a date and wherein an oldest data point is at a center of the helical display or at an outer edge of the helical display and a newest data point is on an opposite end of the helical display from the oldest data point.

7. The data visualization overlay system of claim 1 wherein the facility map is at least one of a 2-dimensional map, a 3-dimensional map, an interactive 3-dimensional map, an augmented reality map, and a video tour map.

* * * * *